US00PP34617P2

(12) United States Plant Patent
Alcock

(10) Patent No.: US PP34,617 P2
(45) Date of Patent: Sep. 27, 2022

(54) ***HEUCHUERA* PLANT NAMED 'ALCHEFRIL'**

(50) Latin Name: ***Heuchera* hybrid**
Varietal Denomination: 'ALCHEFRIL'

(71) Applicant: Neil Alcock, Gwynedd (GB)

(72) Inventor: Neil Alcock, Gwynedd (GB)

( * ) Notice: Subject to any disclaimer, the term of this patent is extended or adjusted under 35 U.S.C. 154(b) by 0 days.

(21) Appl. No.: 17/575,719

(22) Filed: Jan. 14, 2022

Related U.S. Application Data

(60) Provisional application No. 63/150,697, filed on Feb. 18, 2021.

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Karen M Redden
(74) *Attorney, Agent, or Firm* — Penny J. Aguirre

(57) ABSTRACT

A new cultivar of *Heuchera* plant named 'ALCHEFRIL' that is characterized by its foliage with heavily ruffled leaf margins, its very robust, compact plant habit, its leaves that are compounded with deeply lobed leaflets, its globe shaped plant habit, its moderate growth rate, and its flowering stems that are moderate in length.

3 Drawing Sheets

Botanical classification: *Heuchera* hybrid.
Cultivar designation: 'ALCHEFRIL'.

BACKGROUND OF THE INVENTION

The present invention relates to a new and distinct cultivar of *Heuchera* of hybrid origin, botanically known as *Heuchera* 'ALCHEFRIL' and is hereinafter referred to by its cultivar name 'ALCHEFRIL'.

The Inventor discovered the new cultivar May of 2016 as a naturally occurring branch mutation of *Heuchera* 'Tangerine Wave' (not patented) in a container block at his nursery in Waunfawr, Gwynedd, United Kingdom.

Asexual propagation of the new cultivar was first accomplished under the direction of the Inventor by basal cuttings in 2017 in Waunfawr, Gwynedd, United Kingdom. Asexual propagation of the new cultivar by basal cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ALCHEFRIL' as a new and unique cultivar of *Heuchera*.

1. 'ALCHEFRIL' exhibits foliage with heavily ruffled leaf margins.
2. 'ALCHEFRIL' exhibits a very robust, compact plant habit.
3. 'ALCHEFRIL' exhibits leaves that are compounded with deeply lobed leaflets.
4. 'ALCHEFRIL' exhibits a globe shaped plant habit.
5. 'ALCHEFRIL' exhibits a moderate growth rate.
6. 'ALCHEFRIL' exhibits flowering stems that are moderate in length.

The seed parent of 'ALCHEFRIL' differs from 'ALCHEFRIL' in having a larger plant size, flat, non-ruffled foliage, an open, lax and less robust plant habit. 'ALCHEFRIL' can be most closely compared to the *Heuchera* cultivars 'Caramel' (U.S. Plant Pat. No. 16,560) and 'Marmalade' (U.S. Plant Pat. No. 15,945). Both 'Caramel' and 'Marmalade' are similar to 'ALCHEFRIL' in foliage coloration. 'Caramel' differs from 'ALCHEFRIL' in having leaves that are larger in size, a more open plant habit, and less leaves per plant. 'Marmalade' differs from 'ALCHEFRIL' in having smoother foliage, a more open plant habit and less leaf pubescence.

STATEMENT REGARDING PRIOR DISCLOSURES BY THE INVENTOR

The Applicant asserts that no publications or advertisements relating to sales, offers for sale, or public distribution occurred more than one year public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales including disclosures by Concept Plants, Growing Colors, Wayside Gardens, Plantipp, Rush Creek Gardens, Plantagogo, Green Leaf Plants, Floral Daily, Waitrose Garden, Horlings Plants, and The Country Garden & Gifts Online Store.

BRIEF DESCRIPTION OF THE DRAWINGS

The accompanying color photograph illustrates the overall appearance and distinct characteristics of the new *Heuchera*. The photograph was taken of a plant 10 months in age as grown outdoors in a 9-cm container in Boskoop, The Netherlands.

The photograph in FIG. 1 provides a side view of the plant of 'ALCHEFRIL' in bloom.

Figure 1:
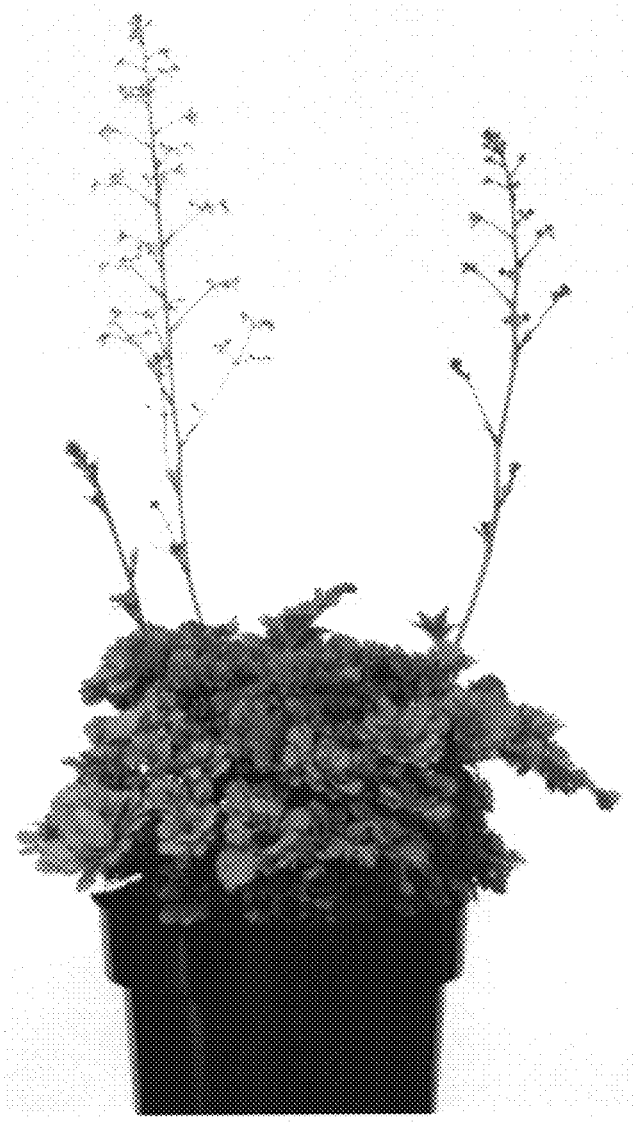
Figure 2:
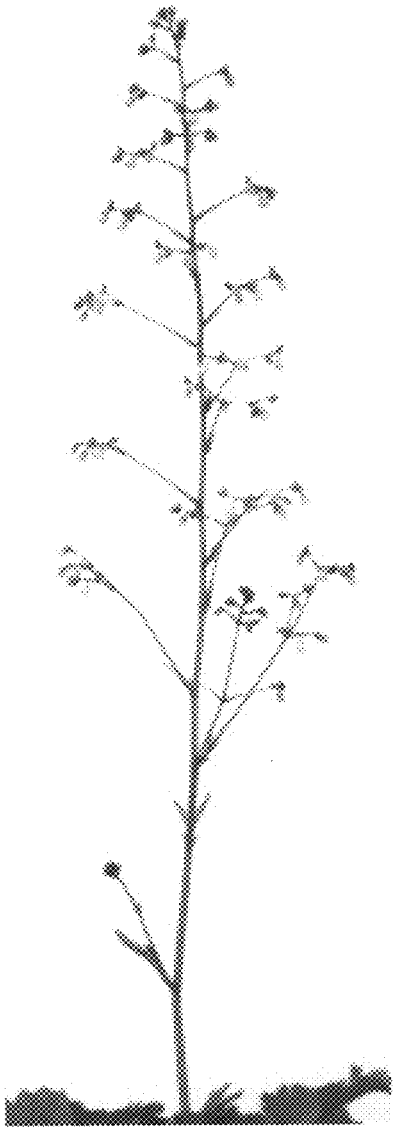

The photograph in FIG. 2 provides a close up of the inflorescence of 'ALCHEFRIL'.

Figure 3:
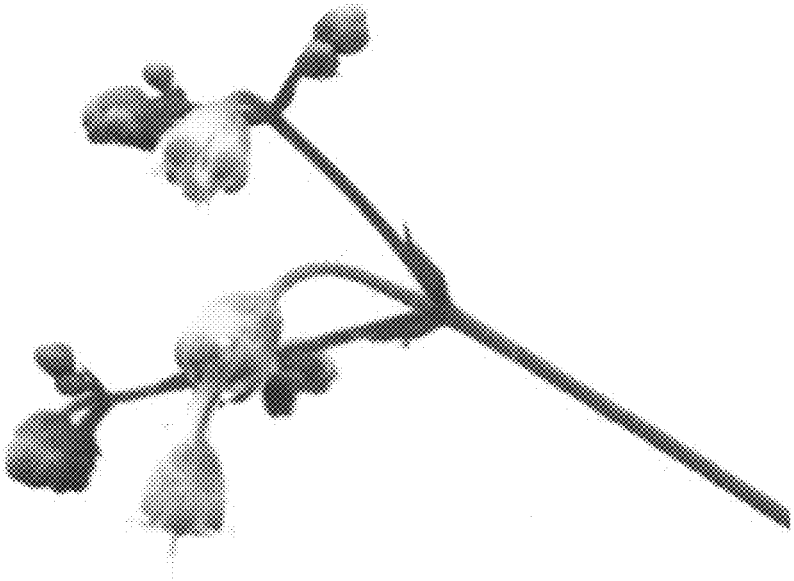

The photograph in FIG. 3 provides a close up of the flowers of 'ALCHEFRIL'.

Figure 4:
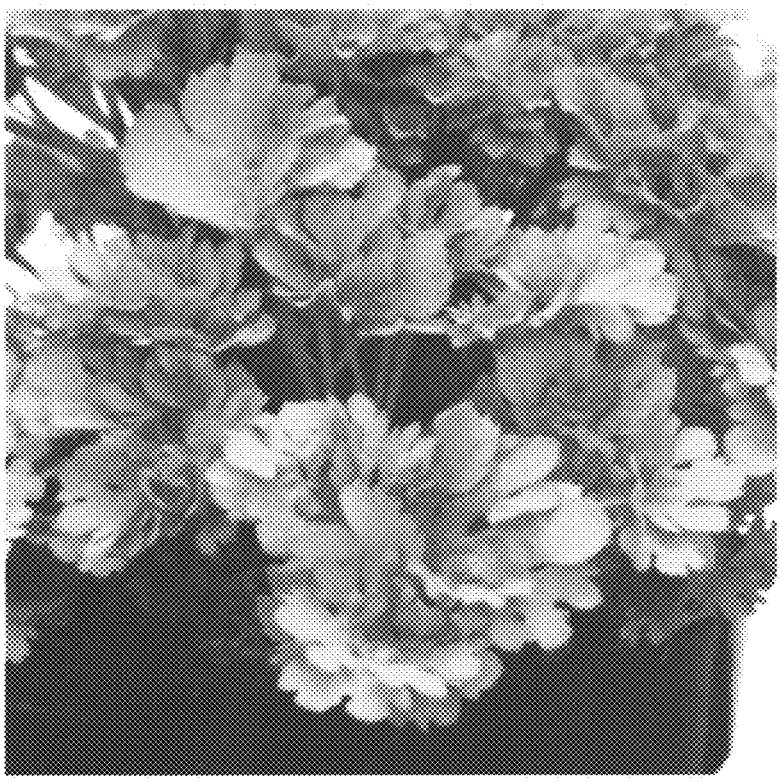

The photograph in FIG. 4 provides a close-up of the foliage of 'ALCHEFRIL'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 10 month-old plants of the new cultivar as grown outdoors in 9-cm containers in Boskoop, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—13 weeks from late spring into summer in United Kingdom.

*Plant type.*—Herbaceous perennial, leaves emerge from rootstock (stemless).

*Plant habit.*—Dense and mounded with inflorescences held upright above the foliage.

*Height and spread.*—An average of 16.9 cm in height (soil level to top of foliar plane), average of 46.3 cm in height (soil level to top of floral plane) and 31 cm in spread.

*Hardiness.*—At least in U.S.D.A. Zones 3 to 9.

*Diseases and pests.*—No susceptibility or resistance to pests or diseases has been observed.

*Root description.*—Fibrous roots on woody rootstalks, 158D in color.

*Propagation.*—Stem cuttings and tissue culture.

*Root development.*—An average of 8 weeks to root a young plant from a stage 3 tissue culture cutting.

*Growth rate.*—Moderately vigorous.

Foliage description:

*Leaf shape.*—Reniform.

*Leaf division.*—Compound, average of 5 leaflets per leaf.

*Leaf attachment.*—Petiolate.

*Leaf arrangement.*—Alternate in basal rosettes.

*Leaf size.*—An average of 14.4 cm in length and 16.4 cm in width.

*Leaf quantity.*—An average of 7 per basal rosette.

*Leaflet size.*—An average of 7.9 cm in length, 7.2 cm in width.

*Leaflet base.*—Acuminate.

*Leaflet shape.*—Broadly ovate, cleft to divided into 5 parts.

*Leaflet apex.*—Short and abruptly acute.

*Leaflet venation.*—Laciniate, upper surface 151A, tinged 182C towards the base, lower surface N148B to N148C.

*Leaflet margins.*—Deeply lobed, an average of 5 lobes, sinuses convergent, lobe margins crispate.

*Leaflet surface.*—Both surfaces; non-rugose, smooth and pubescent, upper surface matte, moderately covered with very short strigose hairs; an average of 0.5 mm in length, NN155D in color, lower surface slightly glossy, moderately covered with very short strigose hairs an average of 1 mm in length, more so on the main veins and secondary veins, NN155D in color.

*Leaflet color.*—Young upper surface; 152B, strongly flushed 182B to 182C at the base, young lower surface; 183B, mature and fall upper surface; 152D, changing to 146C at the base, mature and fall lower surface; 182B.

*Petioles.*—An average of 4.9 cm in length and 4 mm in diameter, moderate strength, upper surface color 184B, lower surface color 183C to 183D, densely covered with very short strigose hairs, average of 1.5 mm in length, NN155D in color, at the base of the petiole is winged; average of 1.2 cm in length, 5 mm in width, margins are finely ciliate, color; upper side 182C, lower side 182C to 182D.

*Petiolules.*—An average of 3.8 cm in length and 2 mm in diameter, moderate strength, upper surface color 199C to 199D, tinged 183D, lower surface color 199C, slightly tinged 182D at the base, densely covered with very short strigose hairs, average of 1.5 mm in length, NN155D in color.

Flower description:

*Inflorescence type.*—Numerous small bell-shaped flowers arranged on panicles on peduncles emerging from a basal rosette.

*Inflorescence size.*—An average of 29.4 cm in height and 9.2 cm in diameter.

*Inflorescence number.*—An average of 3 per plant.

*Inflorescence density of flowers.*—Moderate.

*Flower fragrance.*—None.

*Flower quantity.*—Average of 250 flowers per flowering stem.

*Flower lastingness.*—Average of one week.

*Flower buds.*—Ovate in shape, an average of 2.5 mm in length and 2 mm in diameter, color; 144B, lower half 146C, surface is matte and densely covered with very short glandular hairs; an average of 0.2 mm in length and too small to measure color.

*Flower aspect.*—Nodding to slightly outwardly.

*Flower type.*—Single, campanulate.

*Flower size.*—Average of 4.5 mm in diameter and 5 mm in length.

*Petals.*—Average of 5, rotate arrangement and implanted in the hypanthium at base, oblanceolate in shape, margins entire, apex is acute, base is narrow attenuate, upper and lower surface is glabrous, smooth and matte, an average of 4 cm in length and 0.5 mm in width, when opening and fully open upper and lower surface color; NN155C.

*Calyx.*—Campanulate, sepals fused to hypanthium, 4 mm in length and diameter.

*Sepals.*—An average of 5, lower 62.5% fused into campanulate hypanthium, short oblong in shape, an average of 4 mm in length and 1.2 mm in width, margin is entire and fused into hypanthium, apex is obtuse, color; when opening and fully open upper surface; 155C, upper half 145A, base 144C, when opening and fully open lower surface; between 150D and 157D, upper half 145A, base 144C, both surfaces are matte and densely covered with very short glandular hairs an average of 0.2 mm in length and too small to measure color.

*Peduncle.*—An average of 46.1 cm in length and 2 mm in diameter, 175C to 175D, changing to 197A and 199A at the base, primary flower aspect 30°, secondary peduncle aspect to main peduncle 55°, moderate in strength, surface moderately glossy and densely covered with very short soft glandular hairs; average of 0.1 mm in length and too small to measure color.

*Pedicels.*—An average of 5 mm in length and 0.5 mm in diameter, color; 176B, changing to N144A at the distal end, primary flower aspect straight on top of secondary pedicel, secondary and tertiary flower vertical, moderate in strength, surface is slightly glossy and densely covered with very short soft glandular hairs; average of 0.2 mm in length and too small to measure color.

Reproductive organs:

*Gynoecium.*—Pistils; 2, 2.5 cm in length, stigma; club-shaped, 157D in color, 0.25 mm in diameter, style; an average of 2.25 mm in length and 155C in color, ovary; N144D in color.

*Androecium.*—Stamens; 5, anthers; broadly sagittate in shape, average of 0.3 mm in length and width, 165C to 165D in color, filament; 2 mm in length and NN155A in color, pollen; none detected.

*Seed/fruit.*—No fruit or seeds have been observed to date.

It is claimed:

1. A new and distinct cultivar of *Heuchera* plant named 'ALCHEFRIL' as herein illustrated and described.

* * * * *